(12) United States Patent
Dever et al.

(10) Patent No.: US 8,883,767 B2
(45) Date of Patent: Nov. 11, 2014

(54) LOW ETHER COMPOSITIONS AND DELIVERY APPARATUS

(75) Inventors: Gerald R. Dever, Cordova, TN (US); Eric Chen-nan Su, Collierville, TN (US); William Scott Rogersr, Memphis, TN (US); Robert C. Johnson, Memphis, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 430 days.

(21) Appl. No.: 12/897,476

(22) Filed: Oct. 4, 2010

(65) Prior Publication Data

US 2011/0086109 A1  Apr. 14, 2011

Related U.S. Application Data

(60) Provisional application No. 61/249,788, filed on Oct. 8, 2009.

(51) Int. Cl.
| | |
|---|---|
| A61K 31/60 | (2006.01) |
| A61K 47/00 | (2006.01) |
| A61M 35/00 | (2006.01) |
| B05C 17/01 | (2006.01) |
| B43K 1/06 | (2006.01) |
| B67D 7/60 | (2010.01) |
| A61K 8/67 | (2006.01) |
| A61K 8/97 | (2006.01) |
| A61K 8/27 | (2006.01) |
| A61K 8/36 | (2006.01) |
| A61K 8/368 | (2006.01) |
| A61K 47/08 | (2006.01) |
| A61K 47/44 | (2006.01) |
| A61K 47/10 | (2006.01) |
| A61K 47/38 | (2006.01) |
| A61K 36/29 | (2006.01) |
| A61K 33/30 | (2006.01) |
| A61K 31/197 | (2006.01) |
| A61K 9/70 | (2006.01) |
| A61K 9/06 | (2006.01) |
| A61K 47/14 | (2006.01) |
| A61K 9/00 | (2006.01) |
| A61K 47/06 | (2006.01) |
| A61K 8/365 | (2006.01) |
| A61K 31/19 | (2006.01) |
| A61K 8/73 | (2006.01) |
| A61K 31/375 | (2006.01) |

(52) U.S. Cl.
CPC ............. *A61K 33/30* (2013.01); *A61K 8/676* (2013.01); *A61K 8/97* (2013.01); *A61K 8/27* (2013.01); *A61K 8/36* (2013.01); *A61K 31/60* (2013.01); *A61K 8/368* (2013.01); *A61K 47/08* (2013.01); *A61K 47/44* (2013.01); *A61K 47/10* (2013.01); *A61K 47/38* (2013.01); *A61K 36/29* (2013.01); *A61K 31/197* (2013.01); *A61K 9/7015* (2013.01); *A61K 9/06* (2013.01); *A61K 47/14* (2013.01); *A61K 9/0014* (2013.01); *A61K 47/06* (2013.01); *A61K 8/365* (2013.01); *A61K 8/673* (2013.01); *A61K 31/19* (2013.01); *A61K 8/731* (2013.01); *A61K 31/375* (2013.01); *Y10S 514/944* (2013.01)
USPC .......... 514/159; 514/161; 514/162; 514/163; 514/164; 514/772; 514/785; 514/786; 514/788; 514/944; 604/310; 401/171; 401/265; 222/386

(58) Field of Classification Search
USPC ......... 514/159, 161, 162, 163, 164, 772, 785, 514/786, 788, 944; 604/310; 401/171, 265; 222/386

See application file for complete search history.

(56) References Cited

U.S. PATENT DOCUMENTS

| | | | | |
|---|---|---|---|---|
| 4,149,814 | A | * | 4/1979 | Manwaring ................... 401/186 |
| 4,783,185 | A | | 11/1988 | Erismann et al. |
| 5,433,950 | A | | 7/1995 | Popp |
| 5,525,358 | A | * | 6/1996 | Popp ............................. 424/486 |
| 7,309,185 | B2 | | 12/2007 | Thorpe et al. |
| 2006/0110415 | A1 | * | 5/2006 | Gupta ........................... 424/401 |
| 2007/0020038 | A1 | | 1/2007 | Tani |
| 2007/0048355 | A1 | * | 3/2007 | Perlman ........................ 424/443 |
| 2007/0209133 | A1 | * | 9/2007 | Linzell ......................... 15/209.1 |

* cited by examiner

*Primary Examiner* — John Pak
*Assistant Examiner* — Nathan W Schlientz
(74) *Attorney, Agent, or Firm* — Richard S. Parr; Laura M. Ginkel

(57) ABSTRACT

A low ether gel composition for application to skin comprising a keratolytic agent, in particular salicylic acid, and comprising a nitrocellulose and one or more volatile ingredients, which forms a film on contact with skin adequate to form a protective barrier for the keratolytic agent for a period of time necessary to provide treatment to the skin; methods of treating using such compositions, and dispensers containing such compositions.

10 Claims, 4 Drawing Sheets

US 8,883,767 B2

LOW ETHER COMPOSITIONS AND DELIVERY APPARATUS

This application claims priority to U.S. Provisional Application Ser. No. 61/249,788, filed Oct. 8, 2009. The contents of that application are incorporated in their entirety into this specification by reference.

BACKGROUND

Periodic medication dispensing delivery systems have recently been developed to provide for unit dosage delivery of cosmetic and medicinal products. These systems are designed to be easy to manipulate so as to dispense and apply the medicinal product. These systems include devices such as the pen-type dispensers described in U.S. Pat. No. 7,309,185 and US Published Application No. 2007/0020038, which are said to allow for storage of a cosmetic or medicinal product in a device that also contains an integrated apparatus for application of the product. These devices are said to be useful for a variety of cosmetic or medicinal products including dentifrices, such as tooth gel, tooth paste, mouthwash, mouth rinse, tooth whitener, cosmetics such as mascara and eyeliner, hair care products and/or skin treatment compositions.

Certain topical medicinal/cosmetic compositions that comprise volatile solvents that might make use of such delivery systems have heretofore not been made available in such systems. In particular, these devices could be useful for topical liquid cosmetic or medicinal compositions, except for the fact that the compositions contain large amounts volatile solvents necessary as delivery vehicles for active ingredients and additional agents, such as film forming agents. For example, U.S. Pat. No. 5,433,950 describe certain liquid and gel formulations for treating skin lesions, which formulations contain a flexible collodion vehicle comprising nitrocellulose film forming agent in volatile solvents, primarily diethyl ether. Such compositions can contain active ingredients, such as keratolytic agents, for treatment of skin lesions such as warts, calluses and corns, or other skin disorders such as acne, or psoriasis. Because of the presence of volatile solvents in these formulations any substantial escape of solvent from such a periodic dosing device before first use or between uses will result in the treatment compositions having higher active ingredient concentrations than currently allowed by regulatory agencies.

Thus, there is a need for volatile containing cosmetic or medicinal compositions that maintains acceptable active ingredient concentrations in the compositions when packaged in a periodic dispensing delivery system. Further, there is a need for a film forming medical composition that provides sufficient film forming capabilities yet maintains acceptable active ingredient concentrations in the compositions when contained in a periodic dispensing delivery system. Such compositions will better resist the loss of excessive amounts of volatile solvents which will result in increasing the concentration of the active agents beyond regulatory allowances for such drug products and still form useful treatment films upon application. These and other objectives are provided by the invention more fully described and claimed herein.

All patent and non-patent references cited herein are hereby incorporated in their entirety into this specification by reference thereto. Identification or discussion of any reference in this section or any part of this specification shall not be construed as an admission that such reference is available as prior art to the present application.

SUMMARY OF THE INVENTION

This invention provides a gel composition for topical application comprising salicylic acid or salt thereof in a concentration up to about 17% (w/w), a film forming agent, and one or more volatile ingredients, wherein the composition comprises ether in an amount of between about 3% (w/w) and about 14% (w/w)

The invention further provides a gel composition for topical application comprising salicylic acid in a concentration up to approximately 17% (w/w), a collodion product in an amount between about 5 to about 20% (w/w) and one or more volatile ingredients, wherein the composition comprises ether in an amount of between about 3% (w/w) and about 14% (w/w).

The invention also provides a gel composition for topical application comprising salicylic acid in a concentration up to approximately 17% (w/w) and nitrocellulose in an amount between 0.2 and about 1.0% (w/w).

The invention further provides a gel composition for application to skin comprising a keratolytic agent and comprising a collodion product in an amount between about 5% and 20% (w/w) and one or more volatile ingredients, wherein the composition comprises ether in an amount of between about 3% (w/w) and about 14% (w/w), which forms a film on contact with skin adequate to form a protective barrier for the keratolytic agent for a period of time necessary to provide treatment to the skin.

The invention also provides a gel composition for application to skin comprising a keratolytic agent and comprising a nitrocellulose in an amount between about 0.2% and 1.0% (w/w) and one or more volatile ingredients, wherein the composition comprises ether in an amount of between about 3% (w/w) and about 14% (w/w), which forms a film on contact with skin adequate to form a protective barrier for the keratolytic agent for a period of time necessary to provide treatment to the skin.

The invention also provides a method of treating a skin ailment on a subject comprising applying to the skin a composition of the invention, wherein the composition forms a film on contact with skin adequate to form a protective barrier for salicylic acid for a period of time necessary to provide treatment to the lesion.

The invention further provides a dispenser for administering a composition for treating a skin ailment on a subject wherein the dispenser comprises a gel composition of the invention in a reservoir in communication with a dispensing means and means for retarding evaporation of volatile materials in the composition prior to application to a subject.

DETAILED DESCRIPTION

Figure 1:
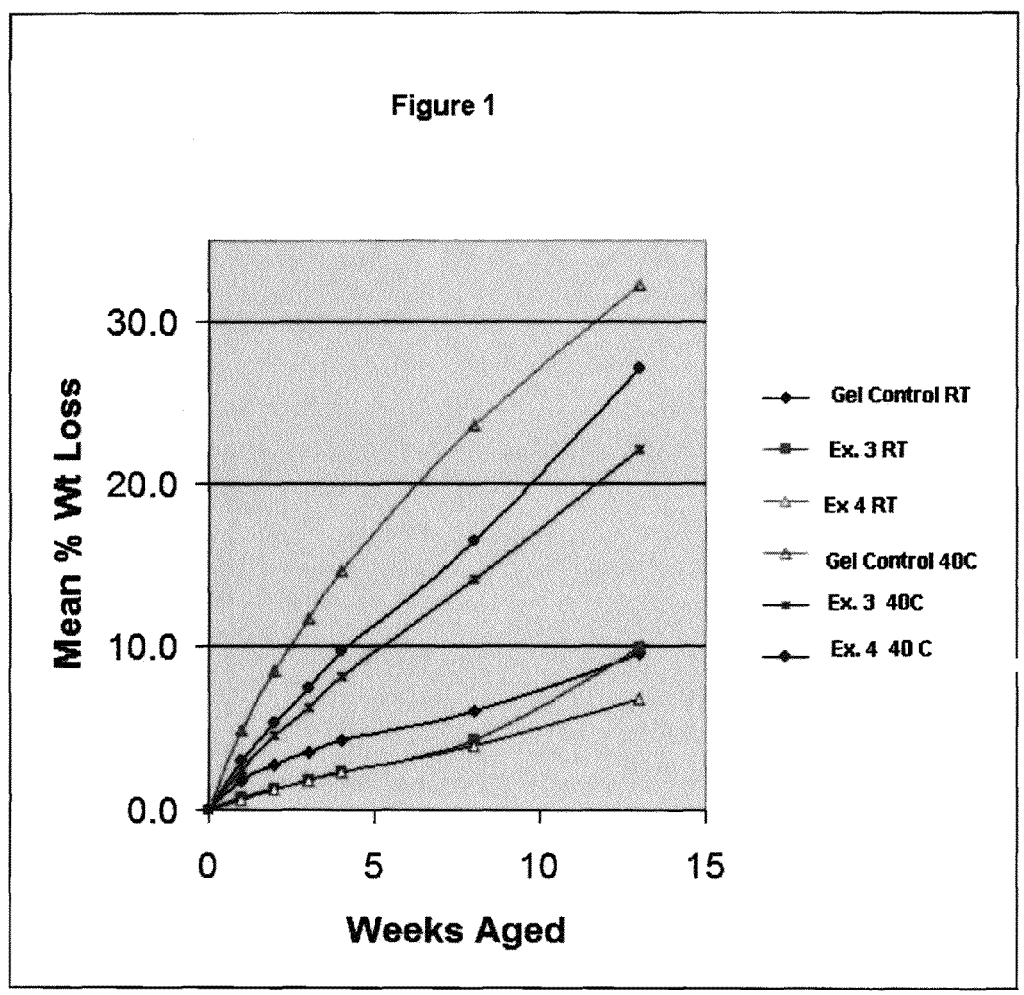
FIG. 1—graph depicting mean percent weight loss of pens filled with control and invention gel formulations held at room temperature (RT) and elevated temperature (40C.) for 13 weeks.

As described herein, the present invention provides enhancements to compositions containing active ingredients and volatile solvents and to delivery devices that store and deliver such compositions. In certain embodiments the compositions also contain film forming agents. The compositions of the invention provide for reduced loss of volatile ingredients when the composition is stored in and applied from such delivery device. In certain embodiments, the device comprises a pen-type delivery system designed to conveniently apply formulations to skin to treat a variety of skin conditions.

Formulations

In one embodiment the invention provides a liquid composition for topical application comprising a cosmetically or medicinally active agent and wherein the composition comprises ether in an amount of between about 3% (w/w) and about 14% (w/w). In certain embodiments, the ether content is between about 6% to about 10% (w/w). In certain embodiments, the ether content is between about 6% to about 7% (w/w). In certain embodiments the ether can comprise an ether useful in cosmetic or medicinal compositions, in particular diethyl ether. In certain embodiments the compositions may contain additional volatile alcohol ingredient can comprise an alcohol useful in cosmetic or medicinal compositions such as methanol, ethanol and propanol, and mixtures thereof.

In certain embodiments, the formulations of the invention are useful to treat skin lesions such as warts, corns and calluses. In other embodiments, the formulations are used to treat other ailments such as acne, psoriasis, dry skin, onychomycosis, ingrown toenails and the like. When formulated as wart treatment product or corn and callus treatment products, certain embodiments of the invention will contain salicylic acid as the active agent. Where the composition is intended to treat disorders or diseases of the nail (i.e. onychomycosis), other active ingredients can be added, such as antifungal agents including clotrimazole, butenafine, terbinafine, miconazole, for example, As used herein, the term "salicylic acid" includes the acid and any salts or esters thereof that are acceptable for use in a topically applied composition. Suitable salts include the sodium, potassium, calcium, lithium or magnesium salts thereof. Suitable esters include the $C_1$ to $C_4$ esters thereof, such as methyl salicylate. Other esters include salsalate (salicylsalicylic acid), the salicylate ester of salicylic acid. Most preferably the acid form is employed as the active ingredient. Salicylic acid is also known as 2-hydroxybenzoic acid. Optionally, other ingredients can be employed in the topical preparation to assist penetration of salicylic acid into the nail and/or skin. Such agents can include nail softeners and avulsers, such as urea, sulfhydryl agents and sulfur-based reducing agents such as sodium sulfide, nail penetration enhancers, and occluding agents and/or hydrophillic fillers to promote hydration of the nail and/or skin.

USFDA Monograph regulations dictate limits of active ingredient concentrations in wart treatment products and corn/callus treatment products to allow for marketing of the product without further agency review. Under such regulations, compositions sold specifying concentrations salicylic acid concentrations are specifically regulated. Thus, in certain embodiments the compositions may contain salicylic acid in an amount up to about 17% (w/w). In certain embodiments the compositions may contain salicylic acid in an amount between about 5% and about 17%. However, the teaching of the subject invention contemplates higher content of salicylic acid in such formulations as one of ordinary skill in the art can prepare despite whether such formulations would fall within the regulations of certain medicinal or cosmetic products.

In other embodiments, the invention further comprises a gel composition for topical application comprising salicylic acid and which contains a collodion product in an amount between about 5 to about 20% (w/w). As used herein the term collodion product includes both collodion and flexible collodion. Collodion products are USP defined formulations comprising nitrocellulose, diethyl ether and ethyl alcohol. Nitrocellulose acts as a film forming agent that protects the active ingredient, here salicylic acid, from evaporation for a period of time sufficient for the active ingredient to effect treatment. Flexible collodion differs from collodion by the addition of camphor and castor oil as plasticizing agents. In certain embodiments the composition will contain a collodion product in an amount between about 5% to about 10% (w/w). Thus, in certain embodiments, the invention provides a liquid composition for application to a skin lesion comprising salicylic acid and comprising nitrocellulose in an between about 0.2% and 1.0% (w/w) wherein the composition forms a film on contact with skin that is adequate to form a protective barrier for salicylic acid for a period of time necessary to provide treatment to the lesion. In certain embodiments the composition may comprise nitrocellulose in an amount between about 0.25% and about 0.50% (w/w).

In certain embodiments, the invention provides a salicylic acid formulation that reduces the amount of the most volatile solvents historically used in these type formulations, such as ethyl ether, which has a boiling point=34.5 C., while still maintaining a viable gel formulation that can be applied dropwise from the periodic unit dosage dispenser on to the surface of a subject in need thereof. Application of salicylic acid formulation from such a device will form a salicylic acid-delivering film on the skin. In certain embodiments, the invention comprises a formulation that contains low amounts of low boiling point solvents, for example, those with boiling points lower than 40C., such as ethyl ether, and comprises higher amounts of higher-boiling point solvents, for example those with boiling points above about 70 C. that still dissolve the film-forming polymers and produce good films when applied to the skin. Examples of such higher boiling solvents include for example, ethyl acetate (boiling point p=77 C.) and isobutyl acetate (boiling point=118 C.).

In certain embodiments, the compositions of the invention may further comprise additional thickening/viscosifying agents. For example, cellulosic polymers such as hydroxypropyl cellulose, including Klucel® HF (Hercules Inc. Aqualon Division Hopewell, Va. USA), can be added in an amount up to about 2.6%. In certain embodiments, the formulations of the invention further comprise reduced amounts of ethyl lactate, which is a plasticizer for both nitrocellulose and hydroxypropyl cellulose, so as to be present in an amount to improve the strength/flexibility of the applied, dried films produced by the formulations.

In certain embodiments, the formulations of the invention may contain additional nitrocellulose in an amount to improve the strength/flexibilty of the applied, dried films. For example, the formulations may contain nitrocellulose from a pyroxylin solution in an appropriate higher boiling point solvent such as ethyl acetate or other alkyl acetates, as mentioned above. Such pyroxylin solutions are commercially available (CAS 9004-70-0) (Alfa Chem, Kings Point, N.Y. USA) and have been used in cosmetic applications such as nail polish and in furniture lacquers. In certain embodiments, the invention may comprise nitrocellulose-compatible polymers to improve the film-forming characteristics, for example Gantrez polymeric materials such as Gantrez ES-425, Gantrez ES 335-I, and Gantrez ES-225 produced by ISP International Specialty Products (Wayne, N.J., USA). These Gantrez polymers are alkyl esters of polymethyl vinyl ether/maleic acid (PVM/MA), including butyl, isopropyl, and ethyl esters of PVM/MA. Those of ordinary skill in the art will recognize that the appropriate PVM/MA polymers will display compatibility with the other polymeric film formers/viscosifying agents in the proposed formulations in order to form good quality, strong, flexible films upon application.

In certain embodiments, the compositions of the invention may comprise a local anesthetic in compounds used for traditional wart therapy, the present invention alleviates the localized discomfort and irritation often associated with the application of keratolytics to the skin. Local anesthetics include, but are not limited to, esters of benzoic acid such as benzocaine, procaine, tetracaine, and chloroprocaine, and amides such as bupivacaine, dibucaine, lidocaine, mepivacaine, prilocaine, and etidocaine. The amount of local anesthetic present will be that which is effective in achieving localized anesthesia in the area to which the composition is applied, generally from about 0.5% to about 15% or more and preferably from 1% to 10% by weight of composition. For lidocaine, for example, the effective range is from about 0.5% to about 4%. With benzocaine, the effective range is from about 5% to about 25%.

Methods of Treatment

The invention further provides methods of treating various skin ailments with the low ether content compositions of the invention. Thus, in certain embodiments the invention provides a method of treating an ailment on a subject comprising applying to the subject a composition comprising a keratolytic agent and comprising nitrocellulose in an amount between about 0.2 and 1.0% (w/w) to the affected area, wherein the composition forms a film on contact with skin adequate to form a protective barrier for the keratolytic agent for a period of time necessary to provide treatment to the affected area. As demonstrated below, gel compositions formulated with the low ether content of the present invention provide surprisingly superior films to prior compositions. It is thus believed the compositions will provide for advances in treatments of disorders that are amenable to treatment with such compositions due to the benefits from enhanced exposure to the active agents from the improved films. In certain embodiments the keratolytic agent may be salicylic acid, ascorbic acid, calcium pantothenate, glacial acetic acid, lactic acid, podophyllum resin, and zinc chloride or combinations thereof. In certain embodiments, salicylic acid may be present in an amount up to about 17%. In certain embodiments salicylic acid may be present in an amount between about 5% (w/w) and 17% (w/w). In certain embodiments, the ailment may comprise a skin lesion such as warts, corns and calluses. In other embodiments, the ailment may comprise acne, psoriasis, dry skin, onychomycosis, or ingrown toenails.

Keratolytic agents are used topically in the treatment of hyperkeratosis and act by softening and destroying the stratum corneum layer of the skin, thereby enhancing desquamation at the site of application. Thus in one aspect the present invention is useful in the treatment of hyperkeratosis using a film-forming fluid composition of the invention comprising a keratolytic agent such as salicylic acid, flexible collodion and a topically acceptable polymer in an amount sufficient to increase the resilience of the film formed will exhibit the improved compliance and improved therapeutic efficacy.

The present invention also includes the method of treating warts which comprises applying to the wart a composition comprising a therapeutically effective amount of at least one composition of the invention. In certain embodiments the method comprises applying a composition of the invention comprising salicylic acid or a salt thereof. Generally, the composition can be applied to the wart daily or for intermittent intervals, such as for two to three times per week. The duration of treatment may vary greatly, depending on the size of the wart.

The present invention further includes a method of treating onychomycosis which comprises applying to a nail a composition comprising a therapeutically effective amount of at least one composition of the invention. Generally, the preparation can be applied to the nail daily or for intermittent intervals, such as for two to three times per week. The duration of treatment can vary greatly, depending upon the degree of severity of the infection, the part of the body where the nail is being treated, the age of the person, the thickness of the nail, the rate of nail growth and the like. Generally, the toenails of a younger person can be expected to receive treatments up to 6 months, whereas the toenails of an older person can be expected to receive treatment up to about one year. These periods reflect the time required for toenails to completely grow out of the toe. Treatment of fingernails can be expected to be faster, since fingernail growth is approximately twice as fast as toenail growth. Effectiveness of the treatment can be evaluated by the subsidence or disappearance of symptoms. Less severe cases where only part of the distal portion of the nail is infected can be expected to require less time for treatment.

Device

The invention further provides a dispenser for administering a composition for treating a skin disorder as described herein wherein the dispenser comprises a liquid composition of the invention in a reservoir in communication with a dispensing means and means for retarding evaporation of volatile materials in the composition prior to application to a subject. In certain embodiments of the invention, the dispenser is in the form of a pen-like device.

In certain embodiments, the dispenser comprises additional means for retarding evaporation of volatile ingredients of the compositions, such as a pouch that is fabricated from barrier films and that is sealed after the dispenser is placed inside. In additional embodiments, the means for retarding evaporation of volatile materials is placement of a sealing mechanism between the reservoir and the dispensing means.

In certain embodiments the invention provides a means to apply salicylic acid containing formulations to a subject in need there of by applying the formulation from a device comprising a reservoir holding the salicylic acid formulation, a dispensing tip for communicating the formulation from the reservoir to the surface of a subject, such as skin or nails or hair surface, and pressure mechanism for forcing the formulation through the dispensing tip. The pressure mechanism can be a plunger operated mechanically by the user or similar mechanism that forces the formulation through an opening in a dispensing tip. The invention also provides for a dispensing device designed to retard evolution of the volatile solvent ingredients out of the pen dispenser system. In certain embodiments the dispensing device comprises a pen-type dispenser with a barrel shaped reservoir containing the salicylic acid, a dispensing tip which retains the formulation in the reservoir until pressure on the reservoir causes the formulation to move through a barrier in the dispensing tip and forms a droplet to be applied to the surface of a subject in need thereof. Pressure can be applied, for example, by use of a plunger that is activated by the subject. The device can optionally contain a cap for enclosing the dispenser tip when not in use. Improvements provided by the current invention include design elements of the pen itself including style and materials of construction of the sealant means. In certain prior art devices the sealant means is an "O" ring located at the plunger end of the pen dispenser opposite the dispensing tip end of the device. In certain embodiments, the invention comprises equipping the device with a plurality of rubber "O" ring-type or equivalent sealant means, made from suitable, solventresistant materials, at the dispenser tip end, to seal off any evolution of volatile formulation ingredients from a filled device. In addition, the device of the invention may comprise one or more solvent barrier film adhesive tapes, for example such as 9792R Aluminum Tape available from 3M (St. Paul, Minn., USA) to seal the joints in the pens, such as between a cap covering the pen dispenser tip and the formulation-filled pen barrel. In certain embodiments, the device of the invention further may comprise encasing the device in secondary packaging, either in combination with, or independent of, the above mentioned formulation modifications, sealants, taping, for example by placing the filled dispenser device in a pouch made from heat-sealable, laminate packaging film, such as a PET/aluminum foil/adhesive material such as those available from Hueck Foils, (e.g., TPMSF005SB) (Wall, N.J., USA).

EXPERIMENTAL

Table 1 shows experimental gel formulations containing 17% w/w salicylic acid that were prepared and compared with two known salicylic acid formulations to determine their ability to withstand volatile evaporation in pen-like dispenser devices. The gel control formulation contains lower collodion amounts, and thus lower ether content, than the liquid control and added alcohol. The experimental gel formulations were designed with lower amounts of collodion than the gel control formulation to further lower the volatile ingredient and decrease evaporation of solvent, yet still produce a viable film upon application to skin. All amounts in the table are listed by percent by weight of formulation. Weight amounts are listed for the flexible collodion components (pyroxylin (nitrocellulose), castor oil, camphor, ethanol, and ethyl ether) based on their weight percent in flexible collodion.

TABLE 1

| Ingredient | Ex 1 | Ex 2 | Ex 3 | Ex 4 | Gel Control | Liquid Control |
| --- | --- | --- | --- | --- | --- | --- |
| Alcohol SDA-40B | 51.60 | 51.60 | 51.60 | 51.60 | 51.60 | 0.00 |
| Ethyl Lactate | 10.00 | 15.00 | 20.00 | 25.00 | 5.00 | 15.00 |
| Indopol L-50 | 0.10 | 0.10 | 0.10 | 0.10 | 0.10 | 0.10 |
| Salicylic Acid USP | 17.00 | 17.00 | 17.00 | 17.00 | 17.00 | 17.00 |
| Collodion, flexible USP | 20.00 | 15.00 | 10.00 | 5.00 | 25.00 | 64.9 |
| (pyroxylin) | 0.98 | 0.74 | 0.49 | 0.25 | 1.23 | 3.19 |
| (castor oil) | 0.60 | 0.45 | 0.30 | 0.15 | 0.75 | 1.95 |
| (camphor) | 0.40 | 0.30 | 0.20 | 0.10 | 0.50 | 1.30 |
| (ethanol) | 4.84 | 3.63 | 2.43 | 1.22 | 6.05 | 15.8 |
| (diethyl ether) | 13.2 | 9.87 | 6.58 | 3.29 | 16.5 | 42.7 |
| Klucel HF | 1.30 | 1.30 | 1.30 | 1.30 | 1.30 | 0.00 |
| Total | 100 | 100 | 100 | 100 | 100 | 100 |

All formulations were prepared in jars using a compressed-air operated mixing motor, a double-blade mixing shaft. Para films are used to cover the opening of the jar during the mixing operation. Alcohol, ethyl lactate and Indopol L-50 were first charged into the jar and mixed for 10 minutes. Then salicylic acid was added into the mixture and mixed for 30 minutes. Next, flexible collodion was added into the mixture and mixed for 10 minutes. Then Klucel HF powder was slowly added into the mixture while mixing over a period of about 3 to 5 minutes and the final mixture is further mixed for 30 minutes to complete the compounding.

Example gel formulations 3 and 4 were chosen for further analysis in comparison to the gel control formulation to determine the effects of formulation on volatile evaporation over time at room temperature and at 40 C. when stored in pen-like dispenser devices. Formulations were loaded into 60 cc syringes which were used to fill the gel solutions into the pen barrels. The pen barrels were sealed with plastic inserts, covered with silicone nose tips and snap fit with caps. The pen samples were aged at room temperature and at 40° C. for 13 weeks. FIG. 1 shows the results of the testing showing that the formulations of the invention provide substantial improvement in the reduction of loss of volatile ingredients over time at both room temperature and elevated temperature conditions.

Figure 2:
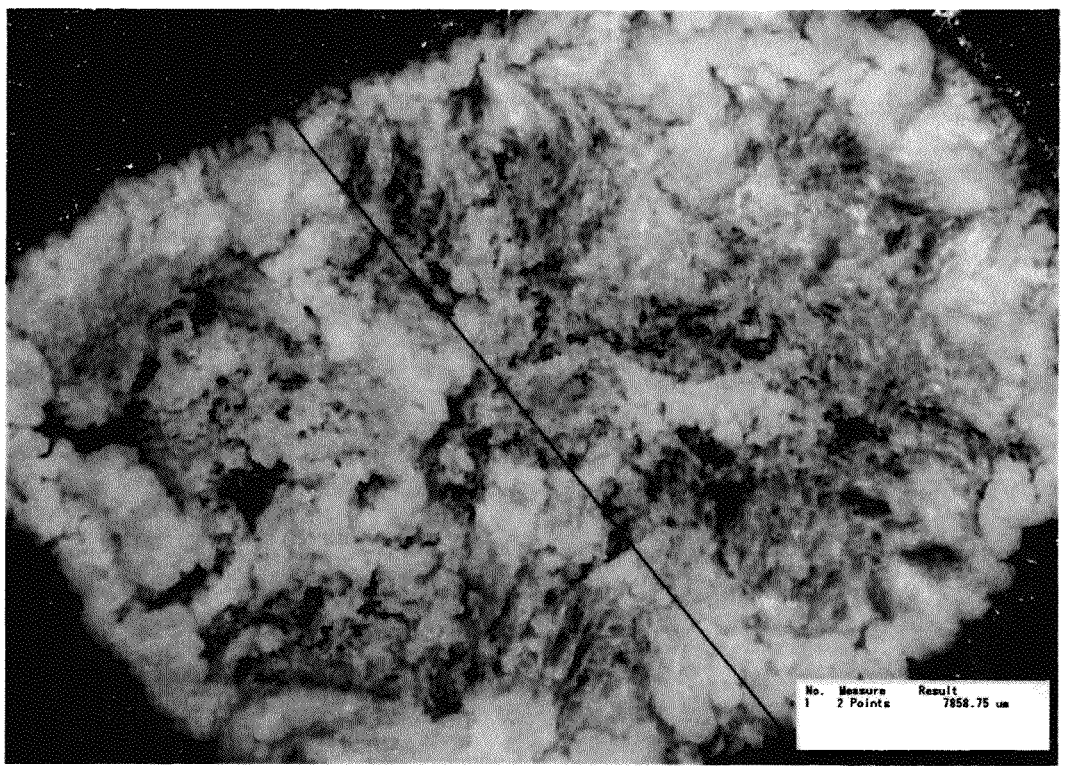
FIG. 2—photomicrograph at 20× magnification showing film formed by liquid control formulation.
Figure 3:
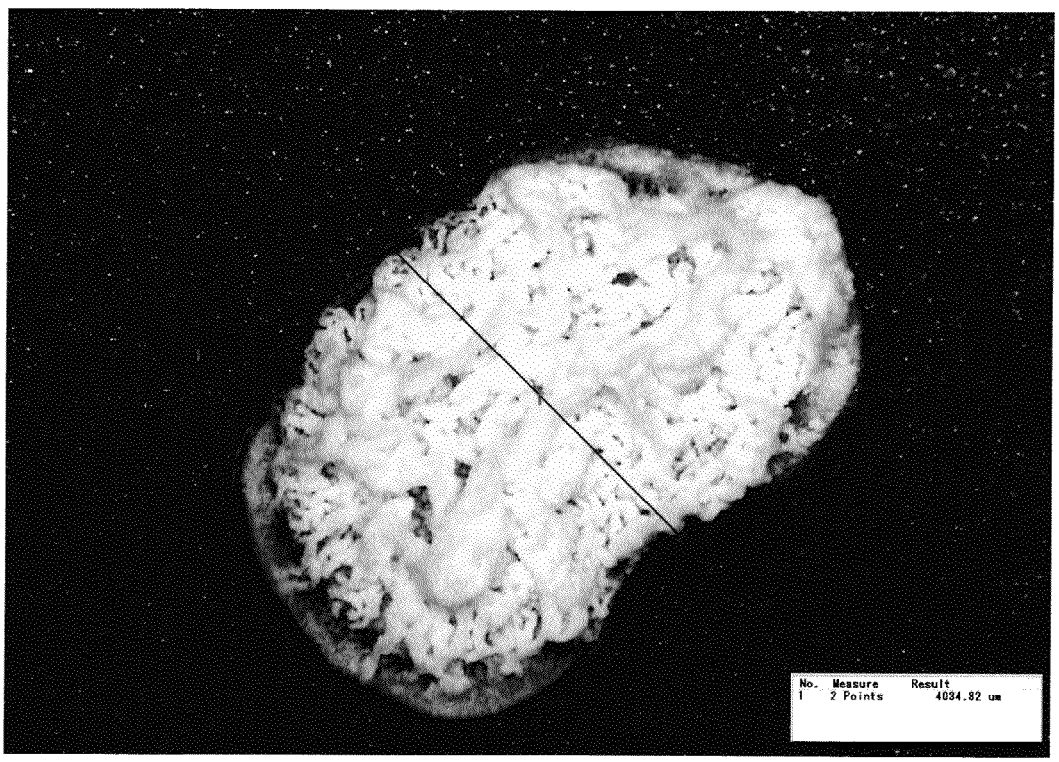
FIG. 3—photo micrograph at 30× magnification showing film formed by gel control formulation.
Figure 4:
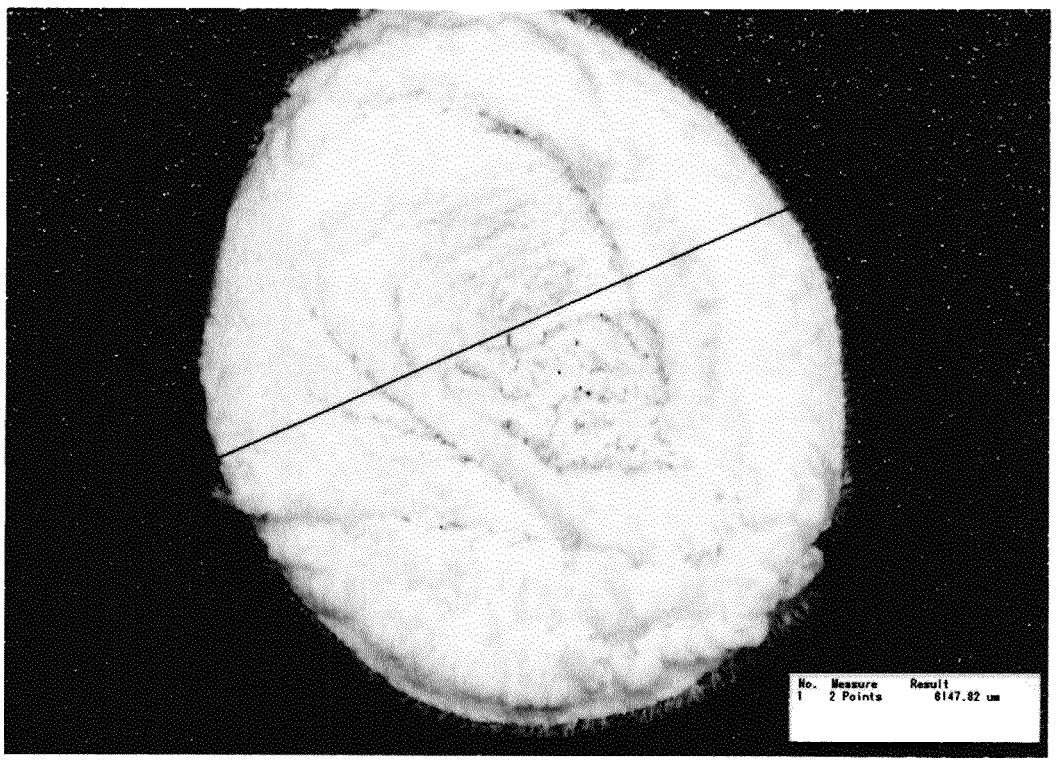
FIG. 4—photomicrograph at 20× magnification showing film formed by invention gel formulation.

Example gel formulation 3 was further subjected to an in vitro film forming test in comparison to the liquid control formulation. FIG. 2 is a photomicrograph of a sample of two drops of the control liquid formulation deposited on a glass microscope slide with an eye dropper, and then dried for several minutes until completely dry. The digital microscopy image was done at magnification 20×. The marker on the micrograph shows that the dried film dot on the glass slide is about 7.5 mm in diameter. FIG. 3 is a photomicrograph of two drops of control gel formulation deposited on a glass microscope slide with an eye dropper, and then dried for several minutes until completely dry. The image was created using the same microscope at 30× magnification. The marker on the micrograph shows that the dried film dot is about 4 mm in diameter. FIG. 4 is a photomicrograph of two drops of example gel formulation 3 deposited on a glass microscope slide with an eye dropper, and then dried for several minutes until completely dry. The image was created using the same microscope at 20× magnification. The marker on the micrograph shows that the dried film dot is about 8.1 mm in diameter.

Comparison of FIG. 2 (liquid control), FIG. 3 (gel control) and FIG. 4 (example formulation 3) show the unexpected benefit in film formation demonstrated by the example formulation of the invention. The dried film dot from the liquid control and gel formulas dry first around the outside circumference of the drops, resulting in a much thicker, "mountain-range-like" film in that area. Because of that, there is substantially less material deposited on the slide in the regions interior to the mountain-range and the films are not uniform in thickness across their area. The control films also demonstrate an aggregated structure of many small micron-sized sub-particles and sub-particle agglomerates. In contrast, the dried film from example gel formulation 3 dries uniformly across its whole surface, not from the edges, and although some larger aggregates of smaller particles are visible, as a whole it is denser and more uniform across its entire area.

What is claimed is:

1. A gel composition for topical application comprising salicylic acid in a concentration of about 17% (w/w), a flexible collodion product in an amount between about 5 to about 10% (w/w), and ethyl lactate in an amount between about 20 to about 25% (w/w), wherein the flexible collodion product comprises 65.8% (w/w) diethyl ether, 24.3% (w/w) ethanol, 2% (w/w) camphor, 3% (w/w) castor oil, and 4.9% (w/w) nitrocellulose.

2. The gel composition of claim 1, further comprising an anesthetic.

3. A wart treatment product comprising the composition of claim 1.

4. A corn/callus treatment product comprising the composition of claim 1.

5. A method of treating a skin ailment on a subject comprising applying to the skin a composition of claim 1, wherein the composition forms a film on contact with skin adequate to form a barrier for salicylic acid for a period of time necessary to provide treatment to the lesion.

6. A dispenser for administering a composition for treating a skin ailment on a subject wherein the dispenser comprises a gel composition of claim 1 in a reservoir in communication with a dispensing means and means for retarding evaporation of volatile materials in the composition prior to application to a subject.

7. The dispenser of claim 6 in the form of a pen-like device.

8. The dispenser of claim 6, wherein the means for retarding evaporation of volatile materials is a pouch that is sealed after the dispenser is placed inside.

9. The dispenser of claim 8, wherein the pouch comprises a barrier film.

10. A method for improving topical delivery of salicylic acid to a subject in need thereof, the method comprising topically administering to the subject the composition of claim 1.

\* \* \* \* \*